(12) United States Patent
Faure et al.

(10) Patent No.: US 9,056,013 B2
(45) Date of Patent: Jun. 16, 2015

(54) SET OF FEMORAL IMPLANTS FOR A KNEE PROTHESIS

(71) Applicant: TORNIER, Montbonnot-Saint-Martin (FR)

(72) Inventors: Eric Faure, Laval (FR); Nicolas Goubet, Bernin (FR); David Dejour, Lyons (FR); Spike Erasmus, Stellenbosch (ZA); Elizabeth Arendt, Minneapolis, MN (US); Julian Feller, Camberwell (AU); Fredrik Almqvist, Ghent (BE)

(73) Assignee: Tornier, Montbonnot-Saint-Martin (FR)

( * ) Notice: Subject to any disclaimer, the term of this patent is extended or adjusted under 35 U.S.C. 154(b) by 42 days.

(21) Appl. No.: 13/923,137

(22) Filed: Jun. 20, 2013

(65) Prior Publication Data
US 2014/0121780 A1 May 1, 2014

Related U.S. Application Data

(60) Provisional application No. 61/662,291, filed on Jun. 20, 2012.

(30) Foreign Application Priority Data

Jun. 20, 2012 (FR) ..................... 12 55798

(51) Int. Cl.
*A61F 2/38* (2006.01)
*A61F 2/30* (2006.01)

(52) U.S. Cl.
CPC ..... *A61F 2/3859* (2013.01); *A61F 2002/30616* (2013.01); *A61F 2002/30828* (2013.01); *A61F 2002/30892* (2013.01); *A61F 2002/3895* (2013.01)

(58) Field of Classification Search
CPC ......... A61F 2/3859; A61F 2/389; A61F 2/30; A61F 2/38; A61F 2/3877; A61F 2/3886; A61F 2002/30
USPC .................. 623/20.14–20.31, 20.35
See application file for complete search history.

(56) References Cited

U.S. PATENT DOCUMENTS 5,226,915 A * 7/1993 Bertin .................. 623/20.15
7,799,084 B2 * 9/2010 Clemow et al. ............ 623/20.15

(Continued)

FOREIGN PATENT DOCUMENTS

| FR | 2728782 A1 | 7/1996 |
| FR | 2908040 A1 | 5/2008 |
| FR | 2955482 A1 | 7/2011 |

OTHER PUBLICATIONS

French Search Report issued in FR1255798 dated Feb. 27, 2013.

*Primary Examiner* — Alvin Stewart
(74) *Attorney, Agent, or Firm* — Knobbe Martens Olson & Bear, LLP

(57) ABSTRACT

A set of femoral implants for a knee prosthesis includes at least two femoral implants having different dimensions from each other. Each femoral implant includes an outer face suitable for cooperating with one of a patellar implant and a patella of a patient, an inner face provided with an anchoring feature for anchoring to a bone of the patient, as well as a distal part and an anterior part each defined both on the outer face and the inner face. The set is characterized in that at least the distal parts of the femoral implants are substantially identical irrespective of the dimensions of the femoral implants.

19 Claims, 4 Drawing Sheets

(56) References Cited

U.S. PATENT DOCUMENTS

| | | | |
|---|---|---|---|
| 8,790,411 B2* | 7/2014 | Mandell | 623/20.35 |
| 2003/0158606 A1* | 8/2003 | Coon et al. | 623/20.15 |
| 2003/0220697 A1* | 11/2003 | Justin et al. | 623/20.15 |
| 2005/0107884 A1* | 5/2005 | Johnson et al. | 623/20.15 |
| 2005/0143833 A1* | 6/2005 | Merchant | 623/20.31 |
| 2005/0154471 A1* | 7/2005 | Aram et al. | 623/20.15 |
| 2008/0058949 A1* | 3/2008 | Dees et al. | 623/20.35 |
| 2009/0281583 A1* | 11/2009 | Brown et al. | 606/86 R |
| 2010/0076567 A1* | 3/2010 | Justin et al. | 623/20.35 |
| 2011/0144760 A1* | 6/2011 | Wong et al. | 623/20.14 |
| 2012/0041566 A1 | 2/2012 | Lenz et al. | |
| 2012/0078263 A1* | 3/2012 | Parisi et al. | 606/89 |
| 2012/0172994 A1* | 7/2012 | Wright et al. | 623/20.18 |
| 2012/0185055 A1* | 7/2012 | Maloney et al. | 623/20.31 |
| 2012/0259335 A1* | 10/2012 | Scifert et al. | 606/80 |
| 2012/0330429 A1* | 12/2012 | Axelson et al. | 623/20.19 |
| 2014/0207243 A1* | 7/2014 | Fitz et al. | 623/20.16 |
| 2014/0228964 A1* | 8/2014 | Lew et al. | 623/20.18 |

* cited by examiner

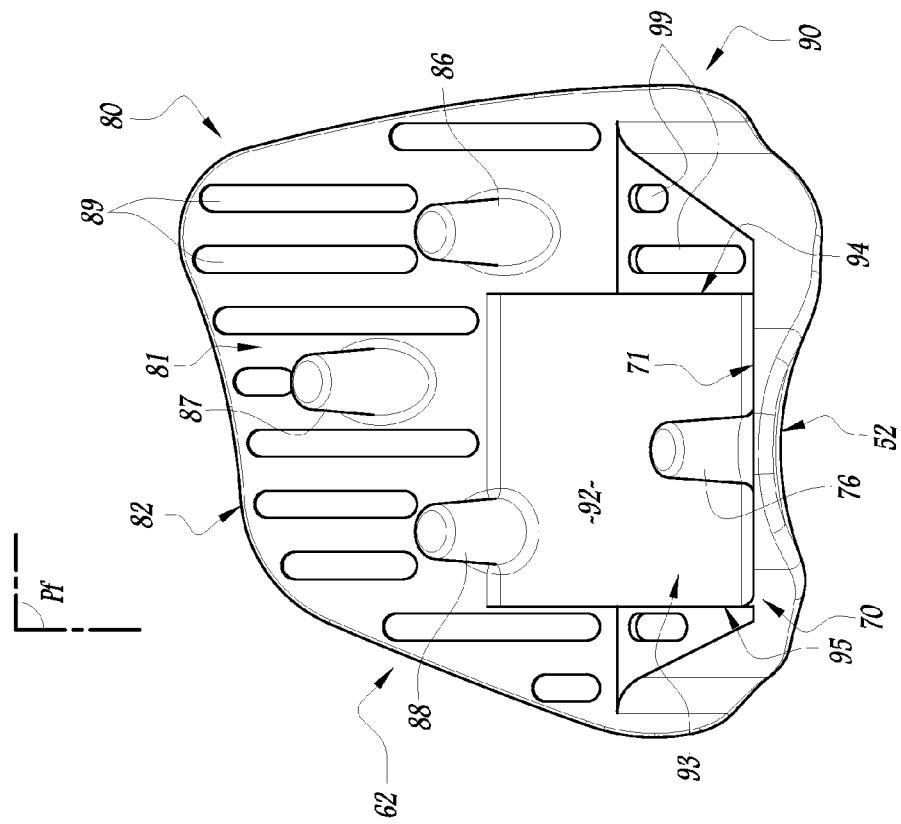
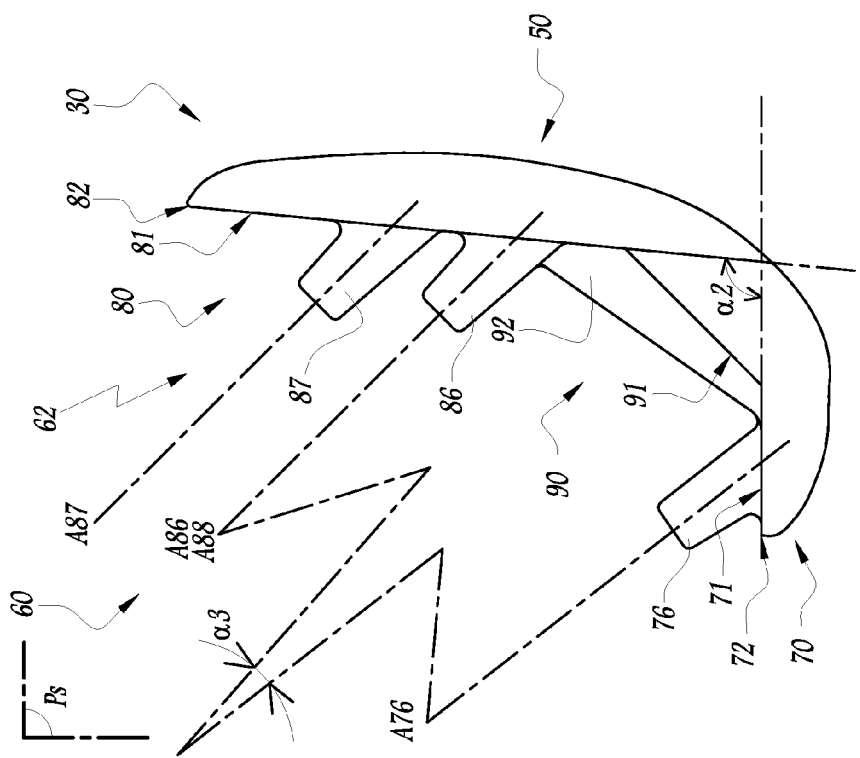

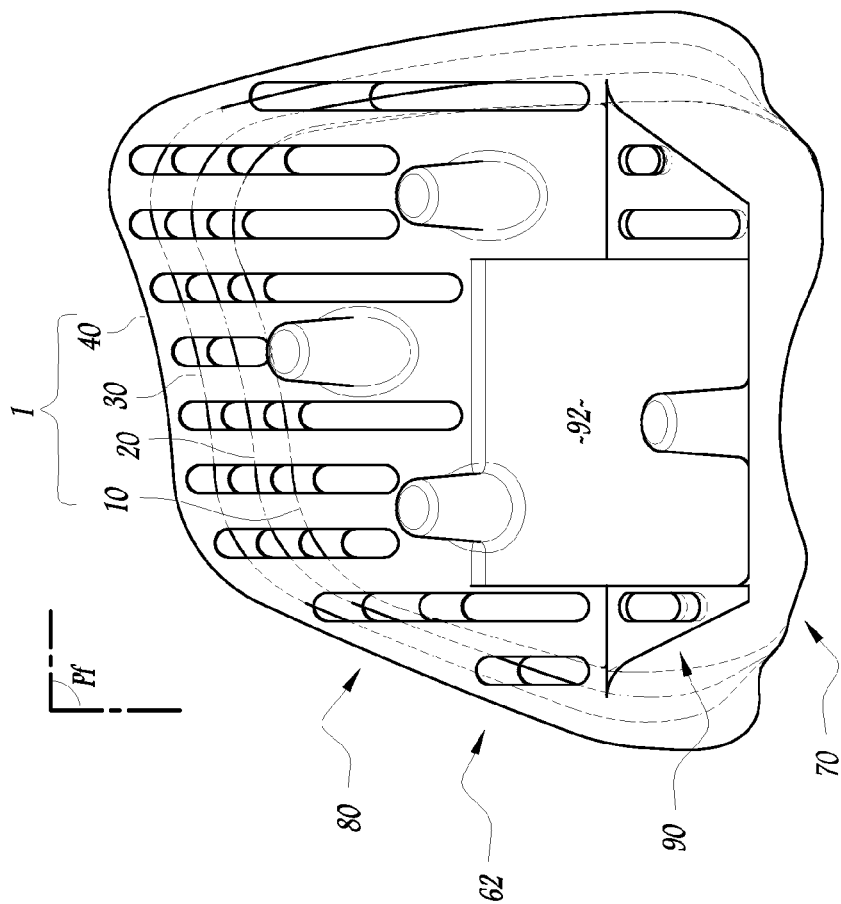
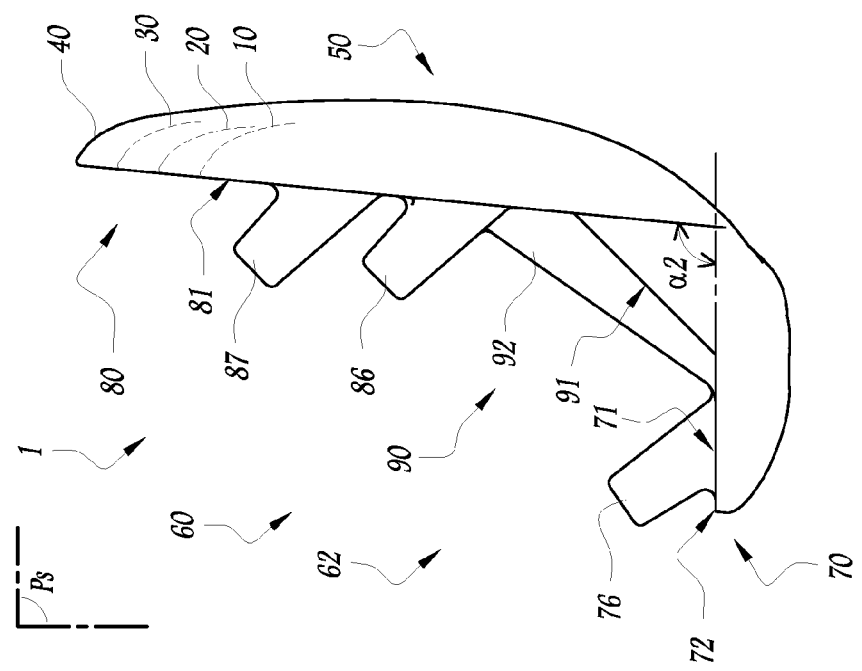

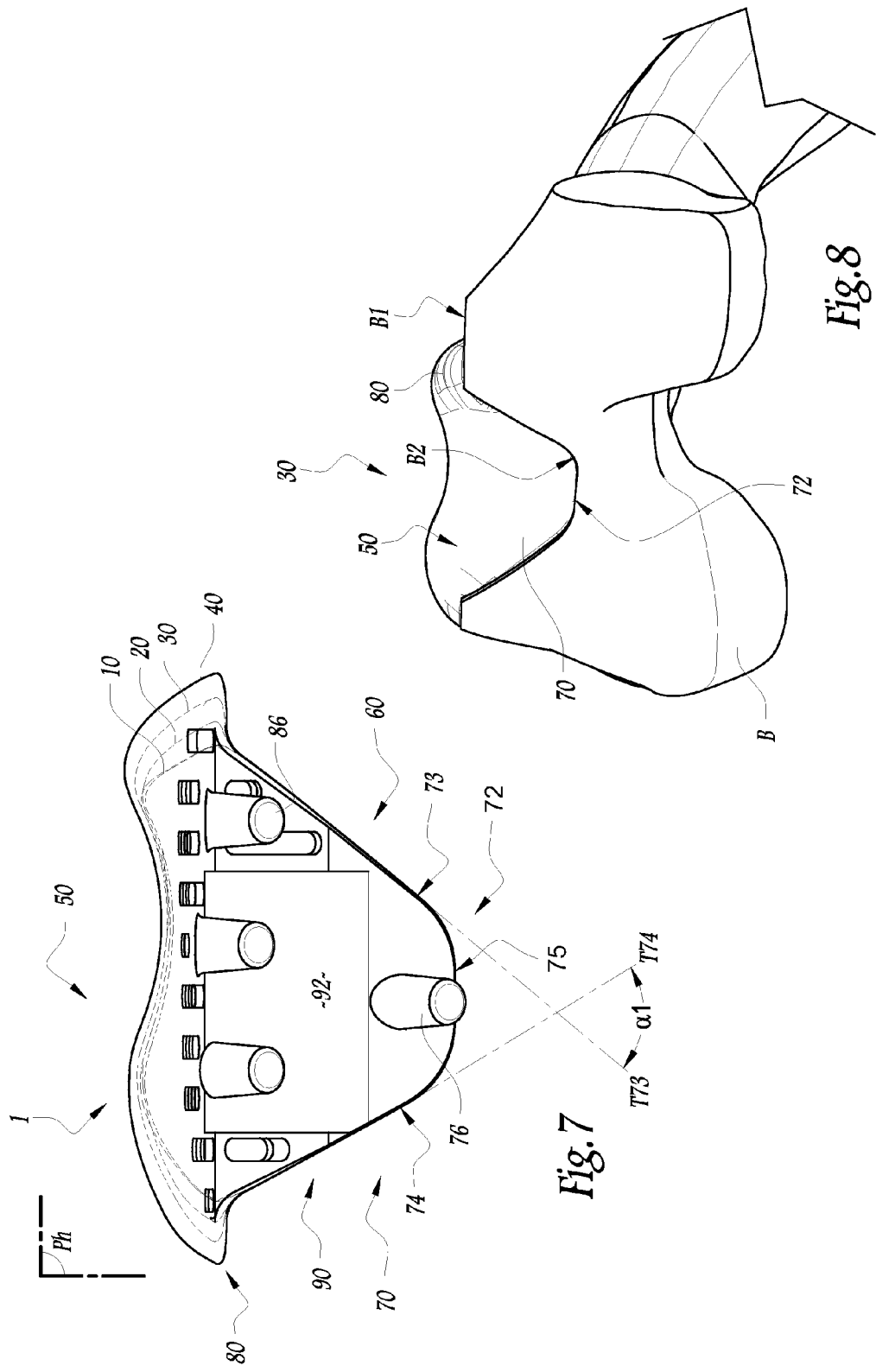

SET OF FEMORAL IMPLANTS FOR A KNEE PROTHESIS

CROSS-REFERENCE TO RELATED APPLICATION

This application claims the benefit of U.S. Provisional Patent Application Ser. No. 61/662,291, filed on Jun. 20, 2012, and FR Patent Application No. 12 55798, filed on Jun. 20, 2012, which are hereby incorporated by reference in their entirety.

TECHNICAL FIELD

The present invention relates to a set of femoral implants for a knee prosthesis. The field of the invention is that of knee prostheses, used when the patient's femur requires a patellofemoral prosthesis.

BACKGROUND

The invention in particular refers to unicompartmental prostheses. In a known manner, such a prosthesis includes a femoral implant capable of cooperating with a patellar implant or a native patella. The femoral implant includes an outer face whereof the profile enables kinematics of the prosthetic knee close to the original kinematics of the knee, as well as an inner face whereof the profile is critical for the positioning and fastening of the implant to the femur. Once placed, this implant undergoes significant mechanical stresses, in particular biasing the fastening on the bone, during the different operating phases: walking, crouching, etc.

Thus, it is essential for the femoral implant to be positioned precisely on the bone requiring repair, then rigidly and lastingly immobilized. These functions are in particular performed by using bone anchoring means formed on the inner face of the implant, and by inserting surgical cement between the inner face and the bone preparation surfaces of the femur.

Before implanting the prosthesis in the patient, the surgeon performs a bone preparation that corresponds on the one hand to the anatomy of the patient, and on the other hand to an available implant profile. More specifically, the implantation of such a prosthesis requires performing distal and anterior bone preparations of the femur. Under these conditions, it is advantageous to have a set of femoral implants having different profiles and dimensions, so as to choose the implant that is best suited to the anatomy of the patient.

However, different implants may require modifying the bone preparation before the suitable implant can be implanted, which causes lost time and may be detrimental to the quality of the surgical operation. In particular, the implantation of the prosthesis is unsatisfactory and may have negative consequences if, due to its profile and dimensions, the implant is not positioned in a configuration where it is flush with the bone preparation surfaces. FR-A-2 908 040 describes a set of femoral implants for a unicompartmental knee prosthesis. These implants are symmetrical and designed to replace only one of the two compartments, inner or outer, of the femur. Thus, these implants have a relatively simple shape compared with a bi-compartmental implant. The thicknesses of these implants, considered at the distal and posterior inner bearing surfaces, are equal and constant irrespective of the dimensions of the implant, while the lengths of the distal and posterior bearing surfaces may vary between the implants. In other words, the distal and posterior parts of the implants have different dimensions for each implant, which is not satisfactory.

U.S. Pat. No. 5,226,915, FR-A-2 728 782 and FR-A-2 955 482 describe other examples of femoral implants.

SUMMARY

The present invention aims to propose a set of improved femoral implants.

To that end, the invention relates to a set of femoral implants for a knee prosthesis, including at least two femoral implants having different dimensions from each other, each femoral implant including:
- an outer face adapted to couple to a patellar implant or a patella,
- an inner face provided with an anchoring feature for anchoring to a bone of the patient,
- a distal part and an anterior part each defined both on the outer face and the inner face, the distal part including a distal inner surface delimited by a first border adapted to be flush with the border of a distal bone preparation, the anterior part including a frontal inner surface defined by a second border adapted to be flush with the border of an anterior bone preparation. At least the distal parts of the femoral implants are substantially identical irrespective of the dimensions of the femoral implants.

Thus, the invention makes it possible to simplify the bone preparation, facilitate positioning of the implant and improve retention thereof during use. Owing to the invention, at least the distal bone preparation is identical for all implants belonging to the set, irrespective of the implant chosen by the surgeon. The initial distal preparation corresponds to the smallest implant of the set. The distal border of the implant is flush with the border of the distal bone preparation; in other words, the implant is positioned alongside the bone thereon. This makes it possible to obtain a good bone-implant transition and prevents any jumping of the patella at the junction of the implant and the bone during a bending-to-extension or extension-to-bending movement. The travel of the patella is improved, which avoids any noise during the transition of the patella between the prosthesis and the distal cartilaginous condyles and prevents wear of the patellar implant or the native patella.

Preferably, in addition to the distal part, other parts of the implants making up the set have the same dimensions and/or the same arrangement from one implant to the next, as described below.

According to other advantageous features of the set of femoral implants according to the invention, considered alone or in combination:
- The distal part of each femoral implant includes a side border and a medial border which, projected in a horizontal anatomical plane, extend along straight lines delimiting a distal angle substantially between 60 degrees and 80 degrees, preferably substantially between 68 degrees and 72 degrees, in particular substantially equal to 70 degrees, the distal angles of the femoral implants being substantially identical irrespective of the dimensions of the femoral implants.
- The anchoring features of the femoral implants have dimensions and a relative position that are substantially identical irrespective of the dimensions of the femoral implants.
- Each femoral implant includes an intermediate part connecting the distal part and the anterior part on the inner face, the intermediate parts of the femoral implants have dimensions and a positioning relative to the distal parts that are substantially identical irrespective of the dimensions of the femoral implants.

For each femoral implant, the intermediate part includes an intermediate surface and a bevel block that is more inclined toward the distal part than the intermediate surface.

For each femoral implant, the anchoring feature includes at least one distal stud and at least one anterior stud that are formed on the inner face, on the distal part and the anterior part, respectively, the studs of the femoral implants having dimensions and a relative positioning that are substantially identical irrespective of the dimensions of the femoral implants.

For each femoral implant, the distal stud and the anterior stud are inclined toward one another on the inner face at an acute angle substantially between 5 degrees and 15 degrees projected in a sagittal anatomical plane.

For each femoral implant, the anchoring feature includes three anterior studs having axes parallel to each other.

Each femoral implant includes a distal inner surface and a frontal inner surface that are inclined relative to one another at an obtuse angle substantially between 90 degrees and 100 degrees, preferably between 94 degrees and 96 degrees, projected in a sagittal anatomical plane.

Each femoral implant is unicompartmental and asymmetrical.

The invention also relates to a surgical method for implanting a knee prosthesis in a patient, the prosthesis including a femoral implant chosen from among a set of femoral implants as mentioned above, the method includes:
  preparing the femur bone including performing at least one anterior cut and distal preparation;
  selecting a femoral implant, the dimensions of which correspond to the femur bone, from among the set of femoral implants; and
  implanting the femoral implant on the femur bone, the distal part being flush with the distal preparation irrespective of the dimensions of the femoral implant.

According to other advantageous features of the surgical method according to the invention, considered alone or in combination:
  The method also includes preparing the inner face of the femoral implant and/or the femur bone using a surgical bone cement, before implanting the femoral implant on the femur bone.
  The method also includes setting the cement, after implanting the femoral implant on the femur bone.
  The method also includes finishing and/or verification and/or equilibration and/or test.

BRIEF DESCRIPTION OF THE DRAWINGS

The invention will be better understood upon reading the following description, provided solely as a non-limiting example and done in reference to the appended drawings, in which:

FIGS. 3 and 4 are elevation views, along arrows III and IV, respectively, in FIG. 2;

FIGS. 5 and 6 are views similar to FIGS. 3 and 4, respectively, showing a set of femoral implants according to the invention, superimposed;

FIG. 7 is an elevation view along arrow VII in FIG. 6; and

FIG. 8 is a perspective view showing a femoral implant, belonging to the set according to the invention, anchored on the right femur of a patient.

DETAILED DESCRIPTION

Figure 2:
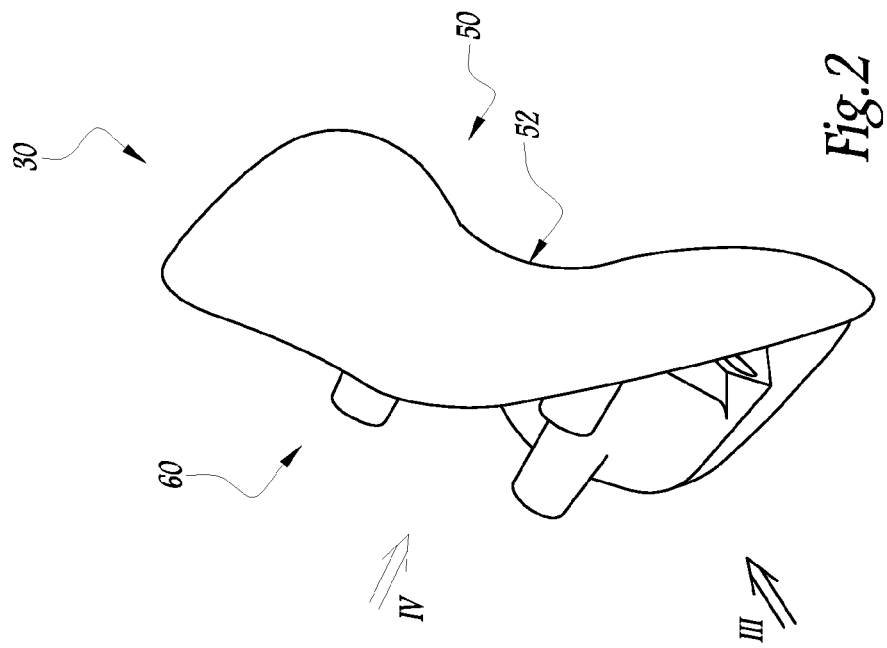
FIG. 2 is another perspective view of the femoral implant of FIG. 1.
Figure 1:
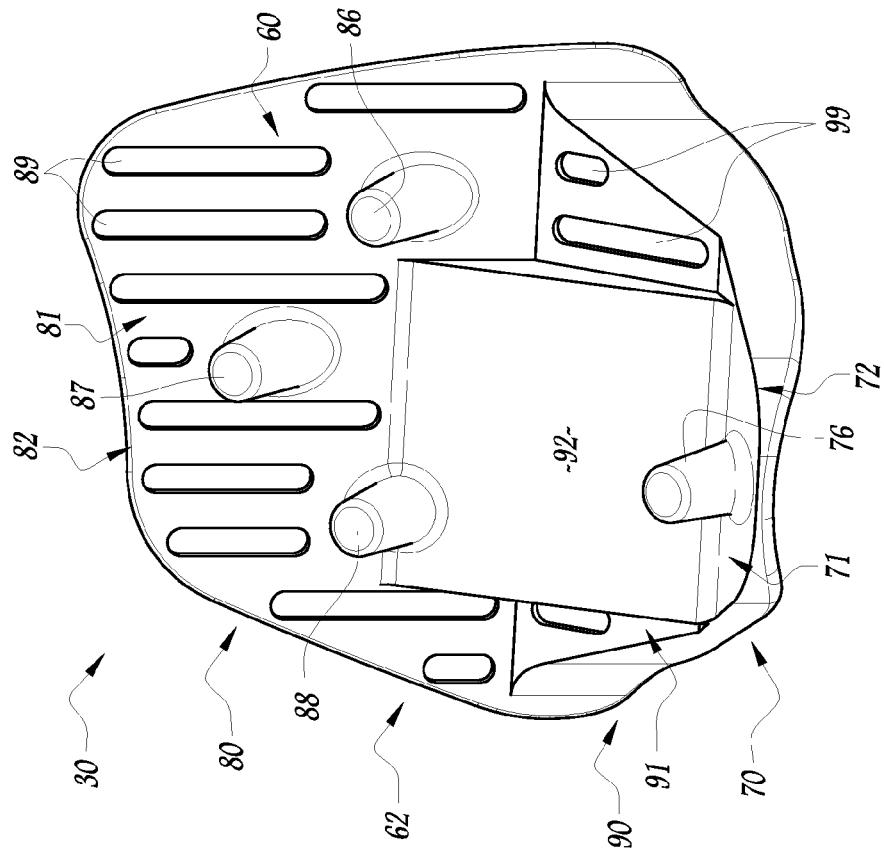
FIG. 1 is a perspective view of a femoral implant, belonging to a set of femoral implants according to the invention and designed to equip the right femur of a patient.

FIGS. 1 to 8 show a femoral implant 30.

This femoral implant 30 belongs to a set 1 of femoral implants 10, 20, 30 and 40, as shown in FIGS. 5 to 7, designed to equip a right femur bone B of a patient, as shown in FIG. 8.

Alternatively, the set 1 may include implants 10-40 suitable for equipping a left femur bone of a patient, or implants suitable for selectively equipping a left femur and a right femur.

Anatomical conventions are used in the present description. In particular, FIGS. 3 and 5 are views in a sagittal anatomical plane Ps, FIGS. 4 and 6 are views in a frontal anatomical plane Pf, and FIG. 7 is a view in a horizontal anatomical plane Ph.

During preparation of the femur bone B, the surgeon performs an anterior bone preparation B1, in this case a bone cut, and a distal bone preparation B2, as shown in FIG. 8. This bone preparation step makes it possible to define bone surfaces corresponding to the profile and dimensions of the femoral implant to be implanted. Furthermore, the surgeon may perform additional cuts or piercings of the bone B, not shown in FIG. 8, to facilitate positioning and fastening of the implant on the bone B.

In practice, the set 1 includes implants 10, 20, 30 and 40 having different profiles and dimensions, such that the surgeon can select the implant 10-40 that is best suited to the anatomy of the patient. Such a set 1 may assume the form of a surgical kit facilitating use thereof by the surgeon. For example, the set may include simple and practical means for identifying each of the implants 10-40 to save time during the surgical operation. This identification may be done using a color code, etching, marking, or any other means suitable for the present application.

According to the invention, the set 1 includes at least two implants having different dimensions. In the example of FIGS. 5 to 7, the implant 10 has the smallest dimensions, the implant 20 has dimensions larger than the implant 10, the implant 30 has dimensions larger than the implant 20, and the implant 40 has the largest dimensions.

The description hereafter refers to the implant 30, with the understanding that the implants 10, 20 and 40 have a comparable configuration, irrespective of their dimensions.

As shown in FIGS. 1 to 4, the femoral implant 30 includes an outer face 50 suitable for cooperating with a patellar implant or a patella of the patient, as well as an inner face 60 provided with means 62 for anchoring to the bone B of the patient, as described below. The outer face 50 includes a trochlear groove 52. The implant 30 also includes a distal part 70 and an anterior part 80, each delimited both by the outer face 50 and the inner face 60. The implant 30 also includes an intermediate part 90 connecting the distal part 70 and the anterior part 80, on the inner face 60 side.

The distal part 70 of the implant 30 includes a distal inner surface 71 delimited by a border 72, as well as a distal stud 76 formed protruding from the surface 71. The border 72 is globally situated at the posterior distal border between the outer face 50 and the inner face 60 at the part 70. More specifically, the border 72 is formed by a side border 73 and a medial border 74 connected by a posterior border 75. The border 72 of the distal part 70 is designed to be flush with the border of the distal bone preparation B2. The stud 76 extends along an axis A76 from the surface 71 on the inner face 60 side.

In the context of the invention, the distal parts 70 of the femoral implants 10-40 are identical, irrespective of the dimensions of the implants 10-40. In particular, the surfaces 71, the border 72 and the stud 76 of the implants 10-40 have the same dimensions and the same arrangement from one implant 10-40 to the next. Thus, all of the implants 10-40 of the set 1 are suitable for the same distal bone preparation B2.

Furthermore, projected in a horizontal anatomical plane Ph, the borders 73 and 74 have a substantially rectilinear profile. In other words, in the plane Ph, the borders 73 and 74 extend along straight lines, T73 and T74, respectively, tangential to the distal part 70. In the plane Ph, the tangents T73 and T74 delimit a distal angle $\alpha 1$ equal to 70 degrees in the example of FIG. 7. Alternatively, the distal angle $\alpha 1$ may be between 60 degrees and 80 degrees, preferably between 68 degrees and 72 degrees. Preferably, as shown in FIG. 7, the distal angles $\alpha 1$ of the femoral implants 10-40 are identical, irrespective of the dimensions of those implants 10-40. Thus, the implant 10-40 selected by the surgeon may be positioned precisely on the bone B, with great precision in the flushness between the border of the distal preparation B2 and the border 72 of the distal part 70.

The anterior part 80 of the implant 30 includes a frontal inner surface 81 defined by a border 82, as well as three anterior studs 86, 87 and 88 protruding from the surface 81. The border 82 is situated globally at the upper border between the outer face 50 and the inner face 60 at the part 80. The border 82 of the anterior part 80 is designed to be flush with the border of the anterior bone cutting B1. The three studs 86, 87 and 88 respectively extend along axes A86, A87 and A88 from the surface 71 on the inner face 60 side. The axes A86, A87 and A88 are parallel to each other. Grooves 89 are formed in the implant 30 at the surface 81.

As shown in FIGS. 5 to 7, the anterior parts 80 of the different implants 10-40 have different dimensions. In other words, the surfaces 81 and the borders 82 have different dimensions from one implant 10-40 to the next. Thus, the surgeon can choose the implant 10-40 whereof the anterior part 80 has the profile that is best suited to the profile of the bone B, and in particular the anterior cutting B1. Likewise, the grooves 89 may have a different configuration for each implant 10-40. However, preferably, as in the example of FIGS. 5 to 7, the studs 86, 87 and 88 have dimensions and a relative positioning that are identical, irrespective of the dimensions of the implants 10-40. Thus, the preparation of the bone anchoring is identical for all of the implants 10-40 of the set 1.

As shown in FIG. 3, the surface 71 and the surface 81 are inclined relative to one another by an obtuse angle $\alpha 2$ between 90 degrees and 100 degrees, preferably between 94 degrees and 96 degrees, projected in the sagittal anatomical plane Ps. Preferably, as shown in FIG. 5, this angle $\alpha 2$ is identical for all of the implants 10-40 of the set 1.

The intermediate part 90 includes an intermediate inner surface 91 connecting the surfaces 71 and 81, as well as an intercondylar bevel block 92 formed protruding on the inner face 60. The bevel block 92 includes a bevel surface 93, a side edge 94 and a medial edge 95. The bevel surface 93 of the block 92 is planar and more inclined toward the distal part 70 than the intermediate surface 91. The edges 94 and 95 extend at a right angle from the surface 91. The block 92 extends partially over the surfaces 71 and 91. Grooves 99 are formed in the implant 30 at the surface 91.

Preferably, as in the example of FIGS. 5 to 7, the intermediate parts 90 of the implants 10-40 have dimensions and a positioning relative to the distal part 70 that are identical, irrespective of the dimensions of those implants 10-40. In other words, the intermediate parts 90 of the implants 10-40 are identical, except for the grooves 99, which may have a different configuration for each implant 10-40.

In the example of the figures, the anchoring means 62 of each implant 10-40 include the studs 76, 86, 87 and 88, as well as the bevel block 92. These means 62 make it possible to fasten the implant 10-40 rigidly to the bone B of the patient, when the distal 70 and anterior 80 parts are respectively positioned against the distal B2 and anterior B1 preparations. To that end, during the bone preparation, the surgeon forms housings, piercings or recesses in the bone B, suitable for receiving each of the anchoring means 62 of the implant 10-40.

As shown in particular in FIGS. 3 and 4, the studs 76, 86, 87 and 88 each have a cylindrical shape converging moving away from the inner face 60, so as to be able to penetrate the housings easily that are provided to that end in the bone B. The distal studs 76 on the one hand, and the anterior studs 86, 87 and 88 on the other hand, are inclined toward one another on the inner face 60 side, by an acute angle $\alpha 3$ between 5 degrees and 15 degrees projected in the sagittal anatomical plane Ps. Thus, when the implant 30 is anchored in the bone B, the presence of this angle $\alpha 3$ reinforces the anchoring strength of the prosthesis.

Preferably, as in the example of FIGS. 5 to 7, the anchoring means 62 of the femoral implants 10-40 have dimensions and a relative positioning that are identical, irrespective of the dimensions of those implants 10-40. Thus, the preparation of the bone anchoring is identical for all of the implants 10-40 of the set 1.

When the surgeon has chosen the implant 10-40 having the profile and dimensions that are best suited to the anatomy of the bone B, for example the implant 30 in FIG. 8, the surgical operation may include a step for preparing the inner face 60 of the implant 30 using a surgical bone cement. The cement is distributed on the surfaces 71, 81 and 91, on the surfaces 93, 94 and 95 of the bevel block 92, in the grooves 89 and 99, and on the studs 76, 86, 87 and 88. Alternatively, only some parts of the inner face 60 receive cement. The grooves 89 and 99 are provided to obtain volumes of cement improving the mechanical shearing strength of the implant 30 at the corresponding surface 81 or 91. Additionally, some cement may also be deposited directly on the bone preparation surfaces B1 and B2.

During positioning and fastening of the implant 30 on the bone B, the anchoring means 62 penetrate the bone B, in particular by impacting the implant 30. Then, the surgical cement inserted between the inner face 60 and the bone preparation surfaces B1 and B2 is compressed between the implant 30 and the bone B. The cement penetrates the cancellous bone B, which improves the anchoring of the implant 30. The surgical operation then includes the step for drying and setting of the cement. Additionally, the operation may also include a finishing and/or verification and/or equilibration and/or test step.

Furthermore, the implants 10-40 of the set 1 may be configured differently from FIGS. 1 to 8 without going beyond the scope of the invention.

In an alternative not shown, the anchoring means 62 may be configured differently from the figures. Preferably, the anchoring means 62 include at least one distal stud 76 and at least one anterior stud 86, 87 and/or 88 formed on the inner face 60 side.

According to another alternative not shown, the intermediate part 90 may include a stiffening rib as a complement or alternative to the bevel block 92.

According to another alternative not shown, the surfaces 71, 81 and/or 91 may have different cement receiving means. For example, the grooves 89 and 99 may be distributed differently. According to another example, the surfaces 71, 81 and/or 91 may include cement receiving basins, which may be provided with raised portions such as pyramids, ribs or grooves.

According to another alternative not shown, each implant 10-40 belonging to the set 1 may be symmetrical. Nevertheless, preferably, each implant 10-40 belonging to the set 1 is unicompartmental and asymmetrical. No matter the embodiment, the distal parts 70 of the femoral implants 10-40 are identical, irrespective of the dimensions of those implants 10-40. Preferably, the implants 10-40 also include other parts whereof the dimensions and relative positioning are identical, i.e., the anchoring means 62, the intermediate part 90, and in particular its bevel block 92.

Furthermore, the technical features of the various embodiments may be combined in whole or in part. Thus, the set of femoral implants is suitable in terms of cost, functionality and performance.

What is claimed is:

1. A set of femoral implants for a knee prosthesis, comprising:
    at least two femoral implants having different dimensions from each other, each femoral implant comprising:
        an outer face adapted to couple to one of a patellar implant and a patella of a patient,
        an inner face provided with an anchoring feature for anchoring to a bone of the patient,
        a distal part and an anterior part each defined both on the outer face and the inner face,
    wherein the distal part includes a distal inner surface delimited by a first border adapted to be flush with a border of a distal bone preparation, the anterior part includes a frontal inner surface defined by a second border adapted to be flush with a border of an anterior bone preparation, and at least the distal parts of the femoral implants are substantially identical irrespective of the dimensions of the femoral implants;
    wherein the distal part of each femoral implant includes a side border and a medial border which, projected in a horizontal anatomical plane, extend along straight lines delimiting a distal angle substantially between 60 degrees and 80 degrees, the distal angles of the femoral implants being substantially identical irrespective of the dimensions of the femoral implants.

2. The set of femoral implants according to claim 1, wherein the distal angle is substantially between 68 degrees and 72 degrees.

3. The set of femoral implants according to claim 2, wherein the distal angle is substantially equal to 70 degrees.

4. The set of femoral implants according to claim 1, wherein the anchoring features of the femoral implants have dimensions and a relative position that are substantially identical irrespective of the dimensions of the femoral implants.

5. The set of femoral implants according to claim 1, wherein the anchoring feature of each femoral implant includes three anterior studs having axes parallel to each other.

6. The set of femoral implants according to claim 1, wherein each femoral implant includes a distal inner surface and a frontal inner surface that are inclined relative to one another at an obtuse angle substantially between 90 degrees and 100 degrees projected in a sagittal anatomical plane.

7. The set of femoral implants according to claim 6, wherein the obtuse angle is substantially between 94 degrees and 96 degrees.

8. The set of femoral implants according to claim 1, wherein each femoral implant is unicompartmental and asymmetrical.

9. The set of femoral implants according to claim 1, wherein each femoral implant includes an intermediate surface and a bevel block that is more inclined toward the distal part than the intermediate surface.

10. The set of femoral implants according to claim 1, wherein a distal stud and an anterior stud of each femoral implant are inclined toward one another on the inner face at an acute angle.

11. The set of femoral implants according to claim 10, wherein the acute angle is substantially between 5 degrees and 15 degrees projected in a sagittal anatomical plane.

12. The set of femoral implants according to claim 1, wherein the anchoring feature of each femoral implant comprises at least one distal stud and at least one anterior stud that are formed on the distal part and the anterior part of the inner face, respectively, the studs of the femoral implants having dimensions and a relative positioning that are substantially identical irrespective of the dimensions of the femoral implants.

13. A set of femoral implants for a knee prosthesis, comprising:
    at least two femoral implants having different dimensions from each other, each femoral implant comprising:
        an outer face adapted to couple to one of a patellar implant and a patella of a patient,
        an inner face provided with an anchoring feature for anchoring to a bone of the patient,
        a distal part and an anterior part each defined both on the outer face and the inner face,
    wherein the distal part includes a distal inner surface delimited by a first border adapted to be flush with a border of a distal bone preparation, the anterior part includes a frontal inner surface defined by a second border adapted to be flush with a border of an anterior bone preparation, and at least the distal parts of the femoral implants are substantially identical irrespective of the dimensions of the femoral implants;
    wherein each femoral implant comprises an intermediate part connecting the distal part and the anterior part on the inner face, the intermediate parts of the femoral implants having dimensions and a positioning relative to the distal parts that are substantially identical irrespective of the dimensions of the femoral implants; and
    wherein the intermediate part of each femoral implant includes an intermediate surface and a bevel block that is more inclined toward the distal part than the intermediate surface.

14. A set of femoral implants for a knee prosthesis, comprising:
    at least two femoral implants having different dimensions from each other, each femoral implant comprising:
        an outer face adapted to couple to one of a patellar implant and a patella of a patient,
        an inner face provided with an anchoring feature for anchoring to a bone of the patient,
        a distal part and an anterior part each defined both on the outer face and the inner face,
    wherein the distal part includes a distal inner surface delimited by a first border adapted to be flush with a border of a distal bone preparation, the anterior part includes a frontal inner surface defined by a second border adapted to be flush with a border of an anterior bone preparation, and at least the distal parts of the femoral implants are substantially identical irrespective of the dimensions of the femoral implants wherein the anchoring feature of each femoral implant comprises at least one distal stud and at least one anterior stud that are formed on the distal part and the anterior part of the inner face, respectively, the studs of the femoral implants having dimensions and a relative positioning that are substantially identical irrespective of the dimensions of the femoral implants; and wherein the distal stud and the anterior stud of each femoral implant are inclined toward one another on the inner face at an acute angle substantially between 5 degrees and 15 degrees projected in a sagittal anatomical plane.

15. The set of femoral implants according to claim 14, wherein each femoral implant includes an intermediate surface and a bevel block that is more inclined toward the distal part than the intermediate surface.

16. A method for implanting a knee prosthesis in a patient, the prosthesis including a femoral implant chosen from among a set of femoral implants, the set of femoral implants including at least two femoral implants having different dimensions from each other, each femoral implant including an outer face suitable for cooperating with one of a patellar implant and a patella of a patient, an inner face provided with an anchoring feature for anchoring to a bone of the patient, a distal part and an anterior part each defined both on the outer face and the inner face, the distal part including a distal inner surface delimited by a first border, the anterior part including a frontal inner surface defined by a second border, at least the distal parts of the femoral implants are substantially identical, the distal part of each femoral implant including a side border and a medial border which, projected in a horizontal anatomical plane, extend along straight lines delimiting a distal angle substantially between 60 degrees and 80 degrees, the distal angles of the femoral implants being substantially identical irrespective of the dimensions of the femoral implant, and the method comprising:

preparing a femur bone of the patient including performing at least one anterior cut and distal preparation;

selecting a femoral implant, the dimensions of which correspond to the femur bone, from among the set of femoral implants; and implanting the femoral implant on the femur bone, the distal part of the femoral implant being flush with the distal preparation irrespective of the dimensions of the femoral implant.

17. The method according to claim 16, further comprising preparing at least one of the inner face of the femoral implant and the femur bone using a surgical bone cement before implanting the femoral implant on the femur bone.

18. The method according to claim 17, further comprising setting the cement after implanting the femoral implant on the femur bone.

19. The method according to claim 16, further comprising at least one of finishing, verifying, equilibrating, and testing the femoral implant.

* * * * *